United States Patent [19]

Meurs et al.

[11] Patent Number: 4,760,160
[45] Date of Patent: Jul. 26, 1988

[54] PREPARATION OF 3-CYANO-4-FLUOROPHENOL

[75] Inventors: Jan H. H. Meurs; David W. Sopher, both of Amsterdam, Netherlands

[73] Assignee: Shell Oil Company, Houston, Tex.

[21] Appl. No.: 818,639

[22] Filed: Jan. 14, 1986

[30] Foreign Application Priority Data

Jan. 25, 1985 [GB] United Kingdom ............... 8501918

[51] Int. Cl.$^4$ .......................................... C07C 121/52
[52] U.S. Cl. ..................................... 558/337; 558/423
[58] Field of Search ............... 558/337, 423; 568/775, 568/377

[56] References Cited

U.S. PATENT DOCUMENTS

3,259,639  7/1986  Taub .................................. 260/396

FOREIGN PATENT DOCUMENTS

902586   8/1962  United Kingdom .
1307841  2/1973  United Kingdom .

OTHER PUBLICATIONS

Buehler et al, "Survey of Organic Synthesis", (1974) p. 275.

Primary Examiner—Anton H. S. Sutto
Attorney, Agent, or Firm—Ronald R. Reper

[57] ABSTRACT

The invention provides a process for the preparation of 4-fluorophenols of formula

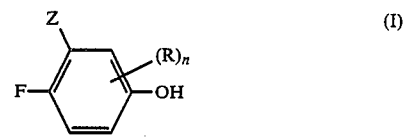

wherein n is 0 to 3, each R independently represents a halogen atom or an alkyl, alkoxy, cyano or optionally substituted amino group and Z represents a hydrogen or halogen atom or a cyano group characterized by reacting a fluorohalocyclohexadienone of formula

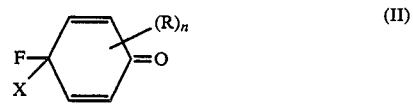

wherein X represents a halogen atom, with a compound of formula A–Z, wherein Z is as defined above and A represents a hydrogen or alkali metal atom, provided that when both A and Z are hydrogen, the reaction is carried out in the additional presence of a Group VIII metal hydrogenation catalyst, and 4-fluorophenols of formula I per se wherein Z is a CN group.

4 Claims, No Drawings

PREPARATION OF 3-CYANO-4-FLUOROPHENOL

BACKGROUND OF THE INVENTION

The present invention relates to a process for the preparation of 4-fluorophenols, and to certain novel 3-cyano-4-fluorophenols preparable thereby.

Fluorophenols are important chemical compounds as they are key intermediates in the synthesis of pharmaceutically or pesticidally active compounds, which in some cases are fluoroanalogues of naturally occurring substances. Fluorophenols are usually prepared by one of two routes:
  (i) from chloronitrobenzenes via halogen exchange, reduction, diazotisation and hydrolysis,
  (ii) from bromofluorobenzenes by hydrolysis.

Since the range of chloronitrobenzenes which undergo the halogen exchange reaction is limited, only a few fluorophenols can be made by route (i) and then at considerable cost. The starting materials for the second route, (substituted-) bromofluorobenzenes, are not readily available. Another process is described in German Auslegeschrift No. 1213848, which specifically discloses the preparation of 4-fluoro-3,5-dimethoxyphenyl by the reduction of 4,4-difluoro-3,5-dimethoxycyclohexadienone using zinc powder and acetic acid. Apart from using the explosive fluoroperchlorate in the preparation of the latter starting material for 3,5-methoxyphenol, the process in its general aspect is limited to starting materials which are substituted with lower alkyl- or alkoxy groups at least one of the two positions meta to the keto group. In addition to use of zinc and acetic acid, the only other reduction conditions disclosed as suitable are chromium(II)-chloride, chromium(II)-acetate or a mixture of sodium iodide and acetic acid.

SUMMARY OF THE INVENTION

According to the invention there is provided a process for the preparation of a 4-fluorophenol of formula

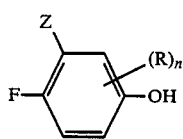
(I)

wherein n is 0 to 3, each R independently represents a halogen atom or an alkyl, alkoxy, cyano or optionally substituted amino group, and Z represents a hydrogen or halogen atom or a cyano group, which process comprises reacting a fluorohalocyclohexadienone of formula

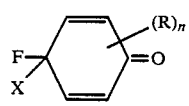
(II)

wherein n and R are as defined above, and X represents a halogen atom, with a compound of formula A-Z, wherein Z is as defined above and A represents a hydrogen or alkali metal atom, provided that when both A and Z represent hydrogen, the reaction is carried out in the additional presence of a Group VIII metal hydrogenation catalyst.

The 3-cyano-4-fluorophenols of formula I (i.e. the compounds of formula I wherein Z is a cyano group), especially 3-cyano-4-fluorophenol, are believed to be novel compounds and per se form an aspect of the invention.

These compounds are extremely versatile starting materials for the preparation of more complex molecules, as the 3-cyano-group may readily be derivatized, by known methods.

DESCRIPTION OF PREFERRED EMBODIMENTS

From the fluorohalocyclohexadienone reactant of formula I, each substituent R may be an alkyl or alkoxy group e.g. a $C_{1-5}$alkyl or alkoxy group, preferably having less than four carbon atoms, especially methyl or methoxy, or a cyano or optionally substituted amino group, e.g. an amino $C_{1-5}$ alkylamino or di($C_{1-5}$alkyl) amino group, or a halogen atom, preferably a chlorine or fluorine atom. R is preferably chlorine or methyl. Preferably n is 0 or 1, most preferably 0.

The other reactant, the compound of formula A-Z, may—according to the choice of A and Z—be hydrogen gas, a hydrogen halide, hydrogen cyanide, or an alkali metal hydride, halide or cyanide. In one specific embodiment A is an alkali metal atom and Z is a fluorine atom or, preferably, a cyano group. In another specific embodiment both A and Z are hydrogen and the Group VIII metal hydrogenation catalyst, which is then required to be present, comprises platinum on a carbon support. Other catalysts suitable for the present process include e.g. palladium or nickel catalysts, in the metallic state, activated or supported on an inert support such as particulate silica, alumina and the like.

The reaction may be carried out by mixing the reactants, conveniently in an inert solvent, and adding the catalyst if necessary, in any order of addition and mixing. Exemplary solvents include alcohols such as methanol, amides such as dimethylformamide, hydrocarbons such as pentane and halogenated hydrocarbons such as dichloromethane. The reaction may conveniently be effected at a temperature in the range 0° to 150° C., preferably 0° to 75° C. Ambient temperatures (e.g. 20°–25° C.) are very convenient. Reaction times in the range from about 5 minutes to 1 hour have been found to give good results. Elevated pressures up to about 100 bar may be used, but are not required.

In the compound of formula II the halogen atom represented by X may be a fluorine, chlorine, bromine or iodine atom, but X preferably represents a fluorine atom because usually the difluoro compound is more economically obtainable. An especially convenient process for the preparation of 4-fluoro-4-halocyclohexadienones is described in U.K. patent application No. 8501917 (Applicant's ref. K-573). When using that method it is possible to carry out the two consecutive reactions without isolating the intermediate fluorohalocyclohexadienone.

Accordingly, in a preferred process of the invention the fluorohalocyclohexadienone of formula II is generated by reacting a compound of formula

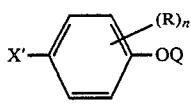

wherein Q represents a hydrogen atom or an alkyl, acyl or aryloxycarbonyl group, X' represents hydrogen or X, and X, n and R are as defined above, with hydrogen fluoride and a Pb(IV) compound, in the presence of a compound which acts as a base towards HF.

The group —OQ may be an —OH group (the compound of formula I being a phenol), an alkoxy group (the compound of formula III being a phenol), an alkoxy group (the compound formula I being a phenol ether), an acyloxy group (a phenol ester), or an aryloxycarbonyloxy group (a phenyl aryl carbonate). The aryl moiety of the aryloxy group is preferably a phenyl group. The substituent Q preferably represents a hydrogen, acetyl or phenoxycarbonyl group.

The Pb(IV) compound may be a Pb(IV) salt, such as $PbF_4$, $PbCl_4$, $Pb(CO_3)_2$ or $Pb(OAc)_4$, or a simple Pb(IV) compounds, such as $PbO_2$, or a salt or oxide containing Pb(IV) compounds, such as $Pb_3O_4$, or a mixture thereof. The Pb(IV) compound may conveniently be a lead oxide, carboxylate, carbonate or fluoride. Preferred Pb(IV) compounds are $PbO_2$, $Pb(OAc)_4$, $PbF_2(OAc)_2$, and, especially, $PbF_4$. As used herein Ac stands for the acetyl group $CH_3.CO$.

If a Pb(IV) compound is not present, but is replaced by a seemingly similar compound such as $MnO_2$, $Mn(OAc)_3$ or $H_2O_2$, no fluorination occurs. Although the precise mechanism of the present reaction is not understood, it is thus clear that the Pb(IV) compound is not simply functioning as an oxidizing agent.

Use of at least one mol of Pb(IV) compound per mol of compound of formula III, and at least two mol per mol when X represents a hydrogen atom, has been found to be very effective.

The compound which acts as a base toward HF, i.e. which can accept protons from HF and/or donate electrons to HF, may conveniently be a fluoride salt; a nitrogen compound of formula $NR^1R^2R^3$, wherein $R^1$, $R^2$ and $R^3$ each independently represent hydrogen or alkyl and/or $R^1$ and $R^2$ together form an alkylene group, or $R^1$, $R^2$ and $R^3$ together form an alkylylidene group; a metal hydroxide or alcoholate; or water. The fluoride salt may be for example be an alkaline earth metal fluoride or, preferably, an alkali metal fluoride, especially KF. It is envisageable to use $PbF_4$ in a double function; both as the Pb(IV) compound and as the compound acting as a base towards HF. The nitrogen compound may be, for example, diethylamine, triethylamine, piperidine, pyridine, or pyrazine. Preferably it is pyridine because the system pyridine/HF is convenient to work with in the laboratory or in industry (low vapour pressure). The metal hydroxide could be an alkali metal hydroxide, optionally in aqueous solution.

Suitably the amount of HF and base should be at least sufficient to provide enough fluorine atoms as needed for the reaction with the phenol compound. Conveniently an excess is used, as this increases the conversion of the (more expensive) phenol compound.

It is not necessary to employ additional solvents or diluents or to work in multiple phase systems. However, when the phenol is more than sparingly soluble in the HF/base system, the reaction is preferably carried out in the additional presence of a liquid diluent which is substantially inert to and immiscible with hydrogen fluoride, for example a liquid aliphatic, optionally halogenated, hydrocarbon, an ether, or a mixture thereof, advantageously dichloromethane or n-pentane.

Reaction of the compound of formula III may conveniently be effected at a temperature in the range from about −30° to 100° C., preferably 0° to 60° C. The reaction may conveniently be effected at ambient temperature, e.g. about 20° C.

The final products of formula I may be used as intermediates in the pharmaceutical or pesticide chemical industry, in the preparation of compounds which in some cases are fluoroanalogues of naturally occurring chemicals.

The invention will be further understood from the following examples.

EXAMPLES

All yields are calculated on the intake of the cyclohexadienone, unless otherwise stated, and are given in molar percentages. The yields were determined by gas/liquid chromatography.

Example 1

4-Fluorophenol from 4,4-difluorocyclohexadienone (a) 400 mg of 4,4-difluorocyclohexadienone, 40 mg of the catalyst (10% platinum on carbon) in 25 ml of methanol were stirred under a hydrogen atmosphere for 10 minutes at 25° C. at atmospheric pressure. p-Fluorophenol was formed in a more than 90% yield.

(b) The above experiment was repeated using Raney-Nickel as the catalyst. After 60 minutes at 60° C. and 35 atm. the yield of p-fluorophenol was 65%.

Example 2

3-Cyano-4-fluorophenol from 4,4-difluorocyclohexadienone

When 2 mmol of 4,4-difluorocyclohexadienone and 4 mmol of potassium cyanide in 0.5 ml of dimethylformamide were mixed for 10 minutes at room temperature, 3-cyano-4-fluorophenol was formed in 90% yield. The spectral data of this new compound are as follows: Mass spectrum: m/e 137 (M+); 109 (M-CO, H); 82; 57.

$^1H$ magnetic resonance spectrum: ($d^7$-DMF): δ4.43(s, 1H); 6.09 (m, 1H); 7.03 (m, 1H) 7.15 (m, 1H).

13C magnetic resonance spectrum: ($d^7$-DMF): δ157.2, 155.8, 123.4, 119.2, 117.6, 114.8, 100.7.

Example 3

4-Fluorophenol from 4-chloro-4-difluorocyclohexadienone prepared from 4-chlorophenol without intermediate isolation 20 mmol of p-chlorophenol in 20 ml of $CH_2Cl_2$ were added over 60 minutes to a stirred mixture of 20 mmol of $PbO_2$, 10 ml of 70% w/w HF in pyridine and 50 ml of $CH_2Cl_2$ at 25° C. The reaction mixture was then stirred for another 60 minutes. Then the organic layer was decanted from the HF-phase and extracted with an equal volume of water. The solvent was distilled off and 10 ml of methanol and 40 mg of the catalyst (10% w/w Pt on C) were added to the residue. This mixture was then stirred under a hydrogen atmosphere for 30 minutes at 25° C. and atmospheric pressure. GLC analysis showed a yield of p-fluorophenol of 20%, based on the intake of p-chlorophenol.

We claim:

1. 3-Cyano-4-fluorophenol.
2. Process for the preparation of a 4-fluorophenol of formula

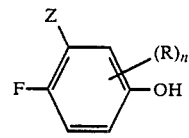

wherein n is 0 to 3, each R independently represents a halogen atom, or an alkyl, alkoxy, cyano group or optionally substituted amino group, and Z represents a cyano group, which comprises reacting at a temperature from about 0° to about 150° C. a fluorohalocyclohexadienone of formula

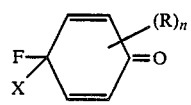

wherein n and R are as defined above and X represents a halogen atom, with a compound of formula A-Z, whrein Z is as defined above and A represents an alkali metal atom.

3. A process according to claim 2 wherein n is 0.
4. A process according to claim 2 wherein the reaction is carried out at a temperature in the range from 0° to 75° C.

* * * * *